United States Patent
Almagro Frutos et al.

(10) Patent No.: US 8,656,914 B2
(45) Date of Patent: Feb. 25, 2014

(54) MEDICAL VENTILATION DEVICE WITH HOSE DETECTION

(75) Inventors: Salvador Almagro Frutos, Helmond (NL); Geert Van Dijk, Well (NL)

(73) Assignee: Dräger Medical GmbH, Lübeck (DE)

( * ) Notice: Subject to any disclaimer, the term of this patent is extended or adjusted under 35 U.S.C. 154(b) by 342 days.

(21) Appl. No.: 12/939,271

(22) Filed: Nov. 4, 2010

(65) Prior Publication Data

US 2011/0120469 A1 May 26, 2011

(30) Foreign Application Priority Data

Nov. 24, 2009 (EP) .................................... 09176829

(51) Int. Cl.
- *A61M 16/00* (2006.01)
- *A62B 7/00* (2006.01)
- *F16K 31/02* (2006.01)

(52) U.S. Cl.
USPC ................................ 128/204.21; 128/204.18

(58) Field of Classification Search
USPC .......................... 128/202.22, 204.18, 204.21, 128/205.23–25; 137/908; 340/286.07
See application file for complete search history.

(56) References Cited

U.S. PATENT DOCUMENTS

| 5,161,525 A * | 11/1992 | Kimm et al. | 128/204.26 |
| 5,797,393 A | 8/1998 | Kohl | |
| 8,210,173 B2 * | 7/2012 | Vandine | 128/204.21 |
| 8,267,084 B2 * | 9/2012 | Kwok | 128/204.21 |
| 2008/0078387 A1 * | 4/2008 | Vandine | 128/204.21 |
| 2010/0078018 A1 * | 4/2010 | Heinonen et al. | 128/202.22 |

FOREIGN PATENT DOCUMENTS

WO  WO 2006092001 A1 * 9/2006

* cited by examiner

*Primary Examiner* — Jackie Ho
*Assistant Examiner* — Mark K Han
(74) *Attorney, Agent, or Firm* — McGlew and Tuttle, P.C.

(57) ABSTRACT

A medical ventilator is coupled to a patient via a hose system to generate a respiratory flow according to a predetermined ventilation mode. The ventilator has a first flow sensor for generating a first sensor signal indicative of an inspiratory flow into the hose system distant from the patient. The hose system has a further flow sensor for generating a further sensor signal indicative of the respiratory flow proximal to the patient. The ventilator has an input for receiving the further sensor signal. The ventilator compares the further sensor signal with an expected sensor signal indicative of the respiratory flow proximal to the patient. The expected sensor signal is determined by a combination of the first sensor signal and the predetermined ventilation mode. The ventilator controls the ventilating in dependence on the comparison.

11 Claims, 3 Drawing Sheets

MEDICAL VENTILATION DEVICE WITH HOSE DETECTION

CROSS REFERENCE TO RELATED APPLICATIONS

This application claims the benefit of priority under 35 U.S.C. §119 of European Patent Application EP 09 176 829.1 filed Nov. 24, 2009, the entire contents of which are incorporated herein by reference.

FIELD OF THE INVENTION

The invention relates to a method of medically ventilating a patient via a hose system. The invention also relates to a medical ventilation device configured for being coupled to a patient via a hose system, to a signal processing system configured for use in the medical ventilation device, and to a data structure on a data carrier for use with a medical ventilation device.

BACKGROUND OF THE INVENTION

Medical ventilation devices (also referred to as ventilators, respiration devices and respirators) are well known. The operation of a medical ventilation device for breathing assistance to a patient is controlled via the pressure or the volume of the respiratory gas. The medical ventilation device has a pressure sensor and a flow sensor in order to make this control effective. With a properly placed flow sensor (usually close to the mouth of the patient), it is possible to measure the inspiratory flow and/or the expiratory flow.

An example of such a portable medical ventilation device is the Oxylog® 3000 manufactured by Dräger Medical A.G. The Oxylog® 3000 offers sophisticated ventilation for patients in emergency situations and during transport in and between hospitals. Designed to support a wide range of patients with various medical conditions, the Oxylog® 3000 offers volume-based and pressure-based operational modes for controlled, synchronized or assisted ventilation. When transporting, e.g., critical-care patients, from the ambulance to the Intensive Care Unit at the hospital, the need of interrupting ventilation therapy is therefore eliminated. Clear flow curves and pressure curves are shown on a high-contrast display, offering reliable patient monitoring.

In operational use, a medical ventilation device is coupled to a patient via a hose system. A medical ventilation device can be configured for operating with different hose systems. Different categories of patients require that different types of hose systems be used. Patients can be categorized on the basis of, e.g., the age of the patient (e.g., young versus adult), and/or the type of medical condition of the patient. An optimum performance of the medical ventilation device requires that the hose system being used match the selected operating mode of the medical ventilation device.

What type of hose system is selected in operational use depends on the type of patient and on the ventilation mode. Also, the type of flow sensor that forms part of the hose system can depend on the type of patient. For these reasons, different types of hose systems are characterized by different combinations of flow sensors and hoses, depending on, e.g., the required accuracy of the measurements of the flow, the hose's resistance to the flow; the hose's compliance; the amount of dead space of the hose; whether the hose is a re-usable hose or a disposable hose, etc. In the case of small children, the tidal volume of the respiratory gas is small and, therefore, the dead space of the hose is very critical.

Therefore, a medical ventilation device is usually optimized and calibrated for use with one or more specific hose systems, and the performance of the medical ventilation device can only comply with the device's specification if these specific hose systems are being used. The use of hose systems, other than the selected hose systems for which the medical ventilation device has been optimized and calibrated, can affect the performance of the medical ventilation device and may even lead to dangerous situations. For example, the pressure of the respiratory gas in the hose system or the volume of the respiratory gas delivered to the patient per unit of time, could become higher than the value set by the operator in the user interface of the medical ventilation device. This is especially a point of attention if the patient is a small child.

There can be various reasons why the hose system being used does not match with the ventilation therapy of the patient in a specific case. One of the reasons may be the following. For example, the medical ventilation device and the hose system have been prepared for a standard-type patient, which is typically an adult patient. If it turns out that the actual patient is a small child instead, this hose system must be replaced by another one prior to use, and the other hose system must be reselected at the medical ventilation device so that the medical ventilation device is properly set. However, in a stressful situation it is easily forgotten to replace and/or reselect the hose system. Another reason may stem from the fact that an operator is less familiar with the ventilation device or is only familiar with a certain type of hose system. If this familiar type of hose system is not the proper one for the set ventilation therapy, a hazardous situation may arise.

Typically, a hose system comprises a hose as a conduit for the respiratory gas, and a flow sensor. The flow sensor of the hose system measures the inspiratory flow and/or the expiratory flow through the hose, and is usually located close to the patient. This flow sensor forms an integral part of the hose system.

For completeness, the expression "dead space" is used, within the context of ventilation therapy, to refer to the volume of gas that is not refreshed for oxygen and for carbon dioxide after exhalation and that is again inhaled by the human body while breathing.

SUMMARY OF THE INVENTION

The invention relates to a method of medically ventilating a patient via a hose system. The method comprises: generating a respiratory flow according to a predetermined ventilation mode; generating a first sensor signal, indicative of an inspiratory flow distant from the patient; generating a further sensor signal indicative of the respiratory flow proximal to the patient; determining an expected sensor signal, indicative of the respiratory flow proximal to the patient on the basis of the first sensor signal and the predetermined ventilation mode; and controlling the ventilating in dependence on the expected sensor signal.

According to the invention, the expected sensor signal is determined by the first sensor signal and the ventilation mode. The ventilation mode in turn determines the type of hose system to be used. The expected sensor signal is used to control the ventilating procedure, based on the first sensor signal representative of the inspiratory flow distant from the patient. More specifically, the expected sensor signal is determined by the first sensor signal and the hose system being used. Tests or experiments conducted in a controlled environment in advance, or calculations carried out in advance, enable a relationship to be defined between the first sensor signal, indicative of the inspiratory flow at one end of the hose system, and the expected sensor signal indicative of the inspiratory flow at the other end of the hose system. Therefore, if both the relationship and the first sensor signal are given, the further sensor signal or a more accurate version thereof, can be derived. The derived further sensor signal is being referred to herein as the "expected sensor signal".

In an embodiment, the further sensor signal is representative of the inspiratory flow proximal to the patient. The controlling comprises: determining a discrepancy between the further sensor signal and the expected sensor signal, and triggering an alarm for drawing attention to the discrepancy if the discrepancy has a magnitude larger than a predetermined threshold. The occurrence of a significant discrepancy may indicate that the hose system being used is not the correct one in view of the ventilation mode, or that the hose system being used is malfunctioning.

In a further embodiment, the further sensor signal is representative of the expiratory flow proximal to the patient. The controlling now comprises: determining a discrepancy between the further sensor signal and the expected sensor signal; and if a magnitude of the discrepancy determined is acceptable according to a predetermined criterion, correcting, under control of the discrepancy, the further sensor signal for controlling the ventilating.

Accordingly, if the discrepancy is not too large, it can be assumed that the correct hose system is being used and is functioning correctly. A predetermined relationship between the first sensor signal and the expected sensor signal can then be used in the pre-determined ventilation mode to control the ventilating.

The first sensor signal is representative of the inspiratory flow, and is measured distant (at a distance) from the patient. The predetermined relationship associates the first sensor signal, representative of the inspiratory flow distant from the patient, with the expected sensor signal that is representative of the inspiratory flow measured proximal to the patient. Assume that the discrepancy between the expected sensor signal and the actual further sensor signal, both in the inspiratory phase of the ventilating, is acceptable. The predetermined relationship, established for the inspiratory flow, can also be used to correct the measurements of the expiratory flow, as represented by the further sensor signal, so as to produce more accurate measurements of the expiratory flow. This more accurate measurement can then be represented, e.g., on a display monitor, to the emergency personnel attending the ventilating.

The expiratory flow proximal to the patient can also be measured by the same further sensor that produced the further sensor signal when indicative of the inspiratory flow proximal to the patient. The further sensor signal, when representative of the expiratory flow, is now corrected, using the predetermined relationship between the first sensor signal, representative of the inspiratory flow, and the further sensor signal when representative of the inspiratory flow. Within this context, reference is made to U.S. Pat. No. 5,797,393, issued to Hans-Joachim Kohl for "Method for controlling the respirating phase in a ventilating apparatus", and is incorporated herein by reference in its entirety. U.S. Pat. No. 5,797,393 discloses a method of controlling a medical ventilation device that accommodates an expiratory flow sensor and an inspiratory flow sensor whose measurements are both being used to control the ventilating of the patient. The current invention can be applied in the scenario disclosed in U.S. Pat. No. 5,797,393 but now using the further flow sensor in the hose system instead of an additional expiratory flow sensor in the medical ventilation device. The measurements of the expiratory flow, obtained via the further flow sensor in the hose system, are now corrected as described above, and used in the medical ventilation device for control of the respirating phase in the manner disclosed in U.S. Pat. No. 5,797,393.

The process of determining the discrepancy and correcting the further sensor signal is, preferably, a recurrent process. For example, the process is executed during every breathing cycle of the patient, or after two or more breathing cycles. Alternatively, the process occurs once per time interval, e.g., once every 10 or 20 seconds, during the ventilating. Alternatively, the process is started each time when the flow of the respiratory gas reaches a certain level, or each time when the rate of change of the flow of the respiratory gas reaches a certain level.

The invention also relates to a medical ventilation device, configured for being coupled to a patient via a hose system. The medical ventilation device is operative to generate a respiratory flow according to a predetermined ventilation mode for ventilating the patient. The medical ventilation device comprises a first flow sensor for generating a first sensor signal indicative of an inspiratory flow distant from the patient. The hose system comprises a further flow sensor for generating a further sensor signal indicative of the respiratory flow proximal to the patient. The medical ventilation device has an input for receiving the further sensor signal. The medical ventilation device comprises a signal processing system configured for: determining an expected sensor signal, indicative of the respiratory flow proximal to the patient, on the basis of the first sensor signal and the predetermined ventilation mode; and controlling the ventilating in dependence on the expected sensor signal.

The ventilation mode determines the type of hose system to be used. The type of hose system to be used can be characterized by a pre-determined relationship between the first sensor signal and the expected sensor signal. That is, given the type of hose system, there is a predetermined relationship between the first sensor signal and an expected sensor signal in the inspiratory phase of the ventilating. Typically, the first flow sensor of the medical ventilation device is much more accurate than the further flow sensor of the hose system. The predetermined relationship enables the production of the expected sensor signal, given the actually generated first sensor signal. Comparing the expected sensor signal with the actually generated further sensor signal provides information about the performance of the medical ventilation device, e.g., whether the correct hose system is being used in view of the predetermined ventilation mode and if so, if the hose system is functioning properly.

An embodiment of the medical ventilation device comprises an alarm unit coupled to the signal processing system. The alarm unit is configured for issuing an alarm to a human operator of the medical ventilation device. Consider the scenario wherein the further sensor signal is representative of the inspiratory flow proximal to the patient. The signal processing system is operative to activate the alarm unit if there is a discrepancy between the further sensor signal and the expected sensor signal, and if the discrepancy has a magnitude larger than a predetermined threshold. A significant discrepancy between the measurements of the inspiratory flow by the first flow sensor and the measurements of the inspiratory flow by the further flow sensor, may indicate that the hose system being used is not the correct one in regard to the ventilation mode, or that the hose system being used is of the correct type but is malfunctioning. The signal processing system activates the alarm if the discrepancy is significant according to some predetermined criterion.

In a further embodiment, the further sensor signal is representative of the expiratory flow proximal to the patient. The medical ventilation device comprises a controller for control of the respiratory flow in accordance with the predetermined ventilation mode. The signal processing system is operative to determine a discrepancy between the further sensor signal and the expected sensor signal. If a magnitude of the discrepancy determined is acceptable according to a predetermined criterion, the signal processing system is operative to correct, under control of the discrepancy, the further sensor signal that is representative of an expiratory flow of the patient. The signal processing system is further operative to control the controller in dependence on the corrected further sensor signal.

The flow sensor in the hose system measures, alternately, the inspiratory flow and the expiratory flow proximal to the patient. The first flow sensor of the medical ventilation device is typically much more accurate than the further flow sensor of the hose system. The hose system is characterized by a predetermined relationship between the first sensor signal and the expected sensor signal. The predetermined relationship is established between the first sensor signal and the further sensor signal that are both indicative of the inspiratory flow. The expiratory flow proximal to the patient is measured by the same further flow sensor that measured the inspiratory flow proximal to the patient. The same predetermined relationship can be used to correct the further sensor signal when being indicative of the expiratory flow so as to produce a more accurate measurement of the expiratory flow proximal to the patient. As specified above, this more accurate measurement can then be represented, e.g., on a display monitor, to the emergency personnel attending the ventilating.

The corrected further sensor signal for the expiratory flow can also be used to control the ventilating. Within this context, reference is made to U.S. Pat. No. 5,797,393, issued to Hans Joachim Kohl for "Method for controlling the respiring phase in a ventilating apparatus", and is herein incorporated by reference. U.S. Pat. No. 5,797,393 discloses a method of controlling a medical ventilation device that accommodates an expiratory flow sensor and an inspiratory flow sensor whose measurements are both being used to control the ventilating of the patient. The current invention can be applied in the scenario disclosed in U.S. Pat. No. 5,797,393 but now using the further flow sensor in the hose system instead of the additional expiratory flow sensor in the medical ventilation device. The measurements of the expiratory flow, obtained via the further flow sensor in the hose system, are now corrected as described above, and used in the medical ventilation device for control of the respirating phase in the manner disclosed in U.S. Pat. No. 5,797,393.

Preferably, the signal processing system executes the task of determining the discrepancy and correcting the further sensor signal in a recurrent fashion. For example, the task is executed during every breathing cycle of the patient, or after two or more breathing cycles. Alternatively, the task occurs once per time interval, e.g., once every 10 or 20 seconds, during the ventilating. Alternatively, the task is started each time when the flow of the respiratory gas reaches a certain level, or each time when the rate of change of the flow of the respiratory gas reaches a certain level.

The invention further relates to a signal processing system configured for use in the medical ventilation device as specified above. Such a signal processing system can be marketed as a component to upgrade medical ventilation devices already in use.

The invention also relates to a data structure on a data carrier (e.g., a semiconductor memory, an optical memory) configured for use with a medical ventilation device. The medical ventilation device is configured for being coupled to a patient via a hose system and is operative to generate a respiratory flow according to a predetermined ventilation mode for ventilating the patient. The medical ventilation device comprises a first flow sensor for generating a first sensor signal indicative of the inspiratory flow distant from the patient. The hose system comprises a further flow sensor for generating a further sensor signal indicative of the respiratory flow proximal to the patient. The medical ventilation device has an input for receiving the further sensor signal. The medical ventilation device comprises a signal processing system configured for determining an expected sensor signal, indicative of the respiratory flow proximal to the patient, on the basis of the first sensor signal and the predetermined ventilation mode; and controlling the ventilating in dependence on the expected sensor signal. The data structure stores data representative of a predetermined relationship between the first sensor signal and the expected sensor signal.

As known, a data structure comprises a physical or logical relationship among data elements, designed to support specific data processing functions. The relationship between the first sensor signal and an expected sensor signal from a flow sensor of a particular hose system characterizes the hose system. As specified above, this relationship can be used to determine raising an alarm or making the measurement of the flow, proximal to the patient, more accurate under control of the first sensor signal. The data structure can be supplied as an aftermarket add-on so as to upgrade or modify an existing medical ventilation device in order to provide the functionality of the medical ventilation device in the invention. The data structure may comprise multiple relationships (each between the first sensor signal and the expected sensor signal) for multiple, different hose systems. Alternatively, the data structure can be provided as an electronic file available from a server on a data network, e.g., the Internet. The server is maintained by, e.g., the manufacturer or the distributor of the medical ventilation device. The electronic file can be downloaded from the server for being installed at the medical ventilation device.

For completeness the following remarks are made. In some embodiments of the invention discussed above, the further sensor signal is representative of the expiratory flow proximal to the patient, and this further sensor signal is corrected under control of a discrepancy between the further sensor signal and an expected sensor signal for control of the ventilating. A similar scenario can be applied if the further sensor signal is representative of the inspiratory flow proximal to the patient. The further sensor signal, being representative of the inspiratory flow proximal to the patient, can also be corrected under control of the discrepancy for control of the ventilating.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
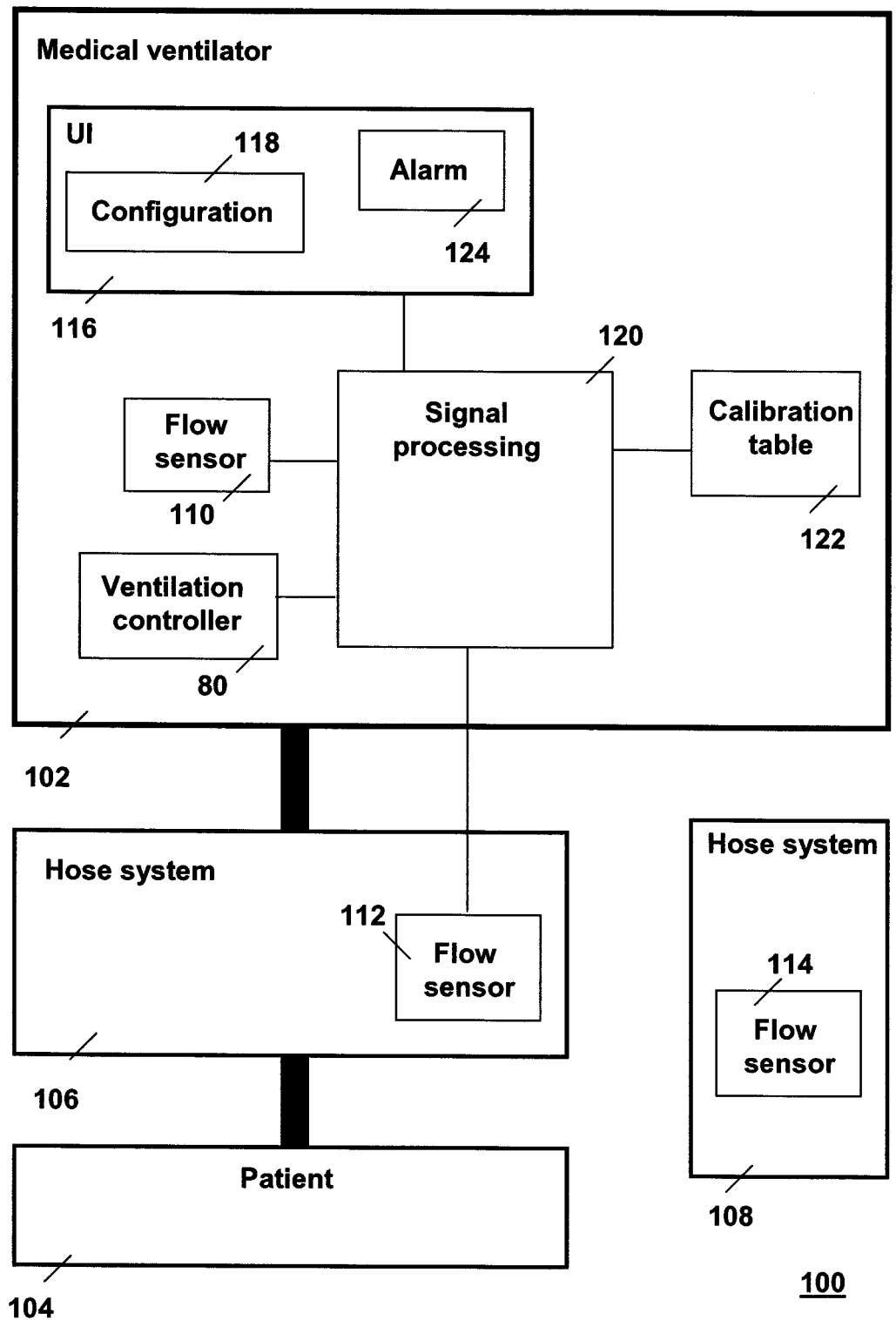
FIG. 1 is a block diagram of system according to the invention.

Referring to the drawings in particular, FIG. 1 is a block diagram of a system 100 according to the invention. The system 100 comprises a medical ventilation device 102 that is coupled to a patient 104 via a specific hose system 106. The specific hose system 106 forms a conduit for a respiratory gas. The medical ventilation device 102 comprises a controller 80, e.g., a microcontroller, which is operative to control a flow of the respiratory gas between the medical ventilation device 102 and the patient 104.

The medical ventilation device 102 is configured for operating with multiple, different hose systems. Each respective one of the multiple, different hose systems is designed for use with a respective category of patients. In order to not obscure the drawing, only a single other hose system 108 has been indicated in FIG. 1. A reason for having different hose systems available with the medical ventilation device 102 is that different categories of patients require that different types of hose systems be used. For example, a child patient may require a hose system that is different from another hose system used with an adult patient. Also, the type of hose system used may be dependent on the type of medical condition of the patient being ventilated. For example, the medical ventilation device 102 is designed for use with any of the following hose systems: a re-useable hose system for an adult (also referred to as arc-usable adult hose system); a disposable hose system for an adult (also referred to as a disposable adult hose system); a re-usable hose system for a small child (also referred to as arc-usable pediatric hose system); a disposable hose system for a small child (also referred to as a disposable pediatric hose system).

The medical ventilation device 102 comprises a first flow sensor 110 for supplying a first sensor signal indicative of the flow of the inspiratory gas, at or near the medical ventilation device 102 in operational use of the medical ventilation device 102. The specific hose system 106 comprises a second flow sensor 112. The other hose system 108 comprises a third flow sensor 114.

If the specific hose system 106 is coupled between the medical ventilation device 102 and the patient 104 in operational use of the medical ventilation device 102, the second flow sensor 112 supplies a second sensor signal indicative of the respiratory flow proximal to the patient 104. The second flow sensor 112 can be used to measure, alternately, the inspiratory flow proximal to the patient 104, and the expiratory flow proximal to the patient 104.

If the other hose system 108 is coupled between the medical ventilation device 102 and the patient 104 in operational use of the medical ventilation system 102, the third flow sensor 114 supplies a third sensor signal indicative of the respiratory flow proximal to the patient 104. The third flow sensor 114 can be used to measure, alternately, the inspiratory flow proximal to the patient 104, and the expiratory flow proximal to the patient 104.

The medical ventilation device 102 comprises a user interface 116 through which the operator of the medical ventilation device 102 selects a specific one of multiple ventilation modes, e.g., through manipulation of one or more dials, switches, etc., (not shown) in a configuration part 118 of the user interface 116, in order to configure the medical ventilation device 102 for operational use. Alternatively, or in addition, the operator may separately set in the configuration part 118 of the user interface 116 the type of hose system being used, e.g., the specific hose system 106 or the other hose system 108. The proper type of hose system to be used can also be determined by the controller 80 of the medical ventilation device 102 on the basis of the ventilation mode selected by the operator in the user interface. As mentioned above different usage scenarios of the medical ventilation device 102, require that different hose systems be used.

The medical ventilation device 102 comprises a signal processing system 120. The signal processing system is coupled to the controller 80 that controls the ventilation process according to the ventilation mode set in the configuration part 118 of the user interface 116. The signal processing system 120 is also coupled to the first flow sensor 110 and to the flow sensor of the hose system being used, here the second flow sensor 112 of the specific hose system 106. The signal processing system 120 is operative to determining an expected sensor signal, indicative of the respiratory flow proximal to the patient 104, on the basis of the first sensor signal and the predetermined ventilation mode. The expected sensor signal is determined by the first sensor signal from the first flow sensor 110 and the type of hose system selected, here the specific hose system 106. The hose system to be used is, in turn, determined by the ventilation mode as set in the configuration part 118 of the user interface 116.

The medical ventilation device 102 is calibrated and optimized for the hose systems, for which the medical ventilation device 102 has been designed to operate. Accordingly, the hose systems are characterized by their performance when connected to the medical ventilation device 102 in operational use.

The signal processing system 120 has access to a calibration table 122, e.g., in the form of a look-up table (LUT), that lists respective performance characteristics for each respective one of the multiple hose systems with which the medical ventilator device 102 has been designed to operate. The performance characteristics have been determined in advance, e.g., by the supplier of the medical ventilation device 102 and of the specific hose system 106 and of the other hose system 108. The performance characteristic of the specific hose system 106 comprises information that enables to determine the expected sensor signal as if it came from the second flow sensor 112, given the first sensor signal from the first flow sensor 110. The performance characteristic of the other hose system 108 comprises information that enables the determination of the expected sensor signal as if it came from the third flow sensor 114, given the first sensor signal from the first flow sensor 110. That is, each respective one of the hose systems with which the medical ventilation device 102 can be used, is characterized by a respective predetermined relationship between the first sensor signal from the first flow sensor 110 and an expected sensor signal from the flow sensor of the respective hose system.

The signal processing system 120 is operative to identify in the calibration table 122 the expected performance characteristic of the expected hose system, based on the information received from the configuration part 118 in the user interface 116. The signal processing system 120 also receives the first sensor signal from the first flow sensor 110 and the second sensor signal from the second flow sensor 112 if the specific hose system 106 is connected to the medical ventilation device 102, or the third sensor signal from the third flow sensor 114 if the other hose system 108 is connected to the medical ventilation device 102. The signal processing system 120 determines the expected sensor signal from the flow sensor in the hose system actually being used and compares the actual sensor signal from the flow sensor in the hose system with the expected sensor signal, in order to detect a discrepancy between the actual sensor signal and the expected sensor signal. If a discrepancy is detected, the signal processing system 120 can intervene in the ventilation process in several manners.

Consider the scenario wherein the specific hose system 106 is connected between the medical ventilation device 102 and the patient 104, and wherein both the first sensor signal and the second sensor signal are indicative of the inspiratory flow. If the discrepancy between the second sensor signal and the expected sensor signal for the specific hose system 106 is significant, e.g., larger than a predetermined threshold, the signal processing system 120 activates an alarm unit 124 in the user interface 116. When activated, the alarm unit 124 of the medical ventilation device 102 issues an audible alarm and/or a visual alarm in order to draw the operator's attention to the discrepancy found. The operator of the medical ventilation device 102 may then verify the settings made in the configuration part 118 of the user interface 116, verify if the patient 104 is ventilated using the correct hose system, and/or verify the integrity of the hose system used, here the specific hose system 106. The integrity of the hose system 106 may have been affected by leakage, blockage, or any other malfunctioning caused by, e.g., material degradation of the hose system 106 as a result of a too long service life. Whether or not the discrepancy determined is significant enough to issue an alarm, depends on the tolerances set in advance in the signal processing system 120, e.g., by the manufacturer of the medical ventilation device 102 or by the operator.

Figure 2:
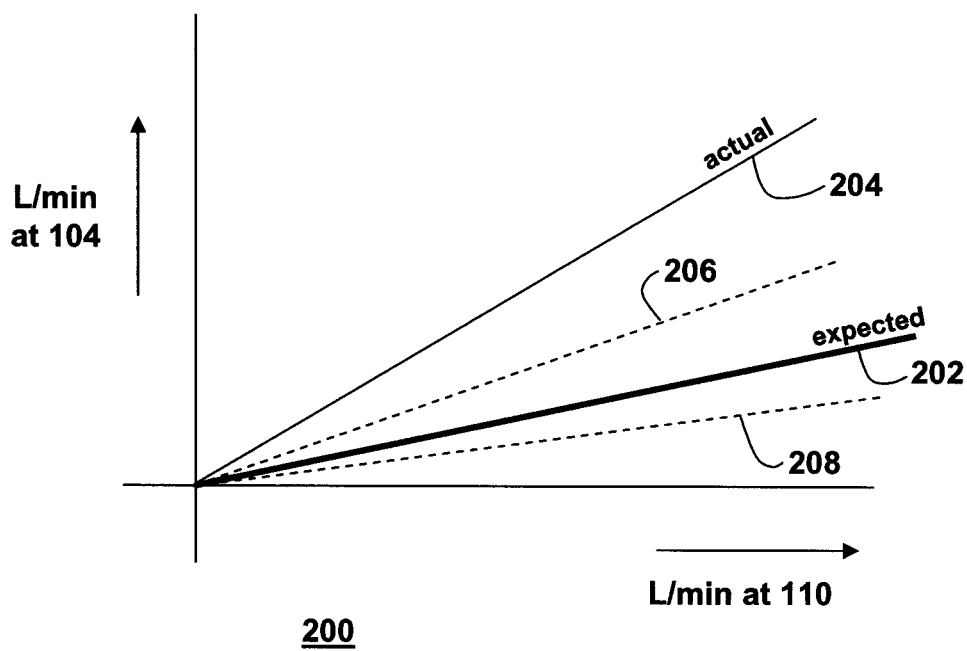
FIG. 2 is a diagram illustrating relationships between flow sensor signals.

Reference is now made to FIG. 2. FIG. 2 is a diagram 200 illustrating an expected relationship 202 between the measurements conducted by the first flow sensor 110 (horizontal) and the measurements (vertical) conducted by the flow sensor in the hose system that is connected to the medical ventilation device 102. As mentioned earlier, the expected relationship has been determined in advance, e.g., through tests conducted on a hose system. The first flow sensor 110 measures the inspiratory flow at one end of the hose system, and the further flow sensor of the hose system measures the inspiratory flow or the inspiratory and expiratory flow at the other end of the particular hose system, i.e., proximal to the patient 104. The expected relationship between the measurements of the inspiratory flow by the first flow sensor 110 and the measurements of the inspiratory flow by the flow sensor in the hose system characterizes the hose system when functioning properly. Accordingly, if the relationship and the measurements of the first flow sensor 110 have been given, the measurements of the inspiratory flow by the flow sensor in the hose system as expected can be derived. The fact, that the relationship 202 is indicated by the qualifier "expected", is based on the particular ventilation mode, selected by the human operator of the medical ventilation device 102 via the configuration interface 118 of the user interface 116. The ventilation mode selected determines the hose system to be used. This expected relationship 202 has been stored in the calibration table 122. The diagram 200 of FIG. 2 also illustrates an actual relationship 204, between the measurements conducted by the first flow sensor 110 (horizontal) and the measurements (vertical) conducted by the flow sensor in the hose system that is actually connected to the medical ventilation device 102. The curve 202 representing the expected relationship is flanked by an additional curve 206 and an additional curve 208 that represent an upper tolerance limit and a lower tolerance limit, respectively, of the measurements as a result of the finite accuracy of the first flow sensor 110 and the finite accuracy of the flow sensor in the hose system being used.

In the example of FIG. 2, the curve of the actual relationship 204 lies outside the parameter region bounded by the additional curves 206 and 208. Accordingly, the signal processing system 120 concludes that there is a significant discrepancy between the expected relationship 202 and the actual relationship 204, as a result of which the signal processing system activates the alarm unit 124.

Figure 3:
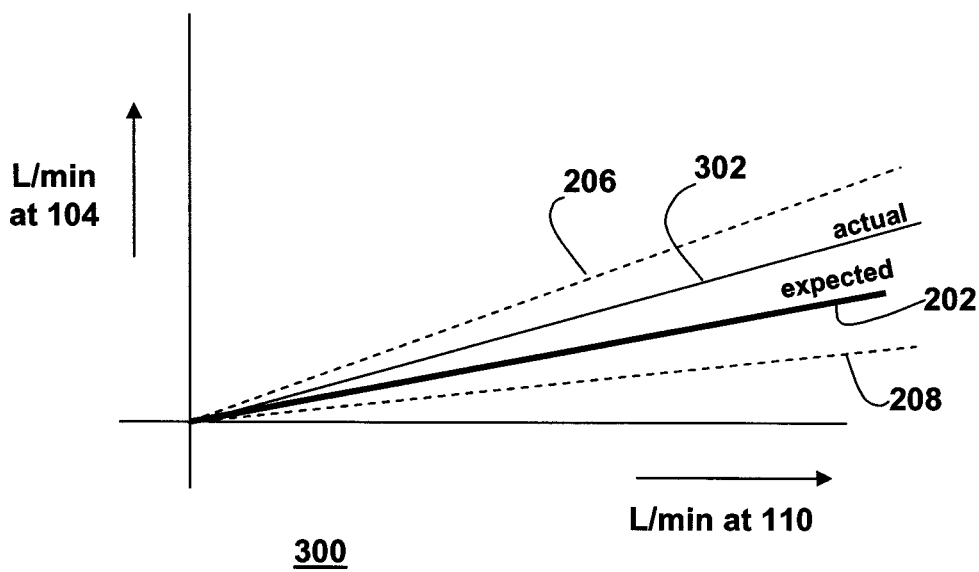
FIG. 3 is another diagram illustrating relationships between flow sensor signals.

Reference is now had to FIG. 3. FIG. 3 is a diagram 300 illustrating the expected relationship 202 between the measurements conducted by the first flow sensor 110 (horizontal) and the measurements (vertical) conducted by the flow sensor in the hose system that is connected to the medical ventilation device 102, as well as an actual relationship 302. Again, the additional curve 206 and the additional curve 208 represent the upper tolerance limit and the lower tolerance limit, respectively, of the measurements as a result of the finite accuracy of the first flow sensor 110 and the finite accuracy of the flow sensor in the hose system being used. Now, the curve of the actual relationship 302 lies within the parameter region bounded by the additional curves 206 and 208. The discrepancy between, on the one hand, the expected sensor signal from the flow sensor in the hose system being used and, on the other hand, the actual sensor signal from the flow sensor in the hose system being used is smaller than shown in the diagram 200 in FIG. 2, and falls within the region of acceptable tolerances, that is bounded by the curves 206 and 208. The signal processing system 120 now concludes that the correct hose system is being used.

Note that the predetermined relationship between the first sensor signal and the further sensor signal of the hose system being used, is based on the inspiratory flow, measured by the first flow sensor 110 distant from the patient 104 and measured proximal to the patient 104 by the further flow sensor of the correct hose system. The correct hose system is the one that matches the ventilation mode set in the configuration interface 118.

Now, the further flow sensor of the correct hose system can also be used to measure the expiratory flow proximal to the patient 104. The measurements of the expiratory flow by the further flow sensor of the correct hose system can now be mapped onto the measurements by the first flow sensor 110 of the inspiratory flow, via the predetermined relationship. As the first flow sensor 110 is more accurate than the further flow sensor in the hose system, the predetermined relationship thus enables to correct the measurements by the further flow sensor of the expiratory flow proximal to the patient. Therefore, in order to generate a more accurate determination of the expiratory flow proximal to the patient 104, the signal processing system 120 uses the expected relationship 202 as stored in the calibration table 122 to generate a corrected version of the measurements of the further flow sensor. The corrected version of the measurements of the expiratory flow can be displayed in the user interface 116 of the medical ventilation device 102 for the information of the operator of the medical ventilation device 102. Alternatively, or in addition, the corrected version of the measurements of the expiratory flow can be used to adjust the operation of the controller 80. See above remark regarding U.S. Pat. No. 5,797,393.

Correction of the measurements of the actual expiratory flow proximal to the patient 104, on the basis of the combination of the first sensor signal produced by the first flow sensor 110 measuring the inspiratory flow and of the expected relationship 202, is activated if the discrepancy between, on the one hand, the expected sensor signal from the flow sensor in the hose system and, on the other hand, the actual sensor signal from the flow sensor in the hose system, lies within the region of acceptable tolerances as bounded by the curves 206 and 208. For practical purposes, one may set a maximum threshold and/or a minimum threshold to the acceptable magnitude of the discrepancy between the expected relationship 202 and the actual relationship 302, for example, in order to avoid corrections on noise levels. The magnitude of the minimum or maximum thresholds may be dynamic in the sense of depending on the currently registered magnitude of the first sensor signal from the first flow sensor 110.

Whether or not the discrepancy is acceptable, depends on the tolerances set in advance in the signal processing system 120, e.g., by the manufacturer of the medical ventilation device 102 or by the operator.

For completeness, it is remarked here that, although the curves 202, 204, 206, 208 and 302 have been indicated as straight lines by way of example, it is clear that the relationships and maximum tolerances represented by these curves are in general non-linear.

Figure 4:
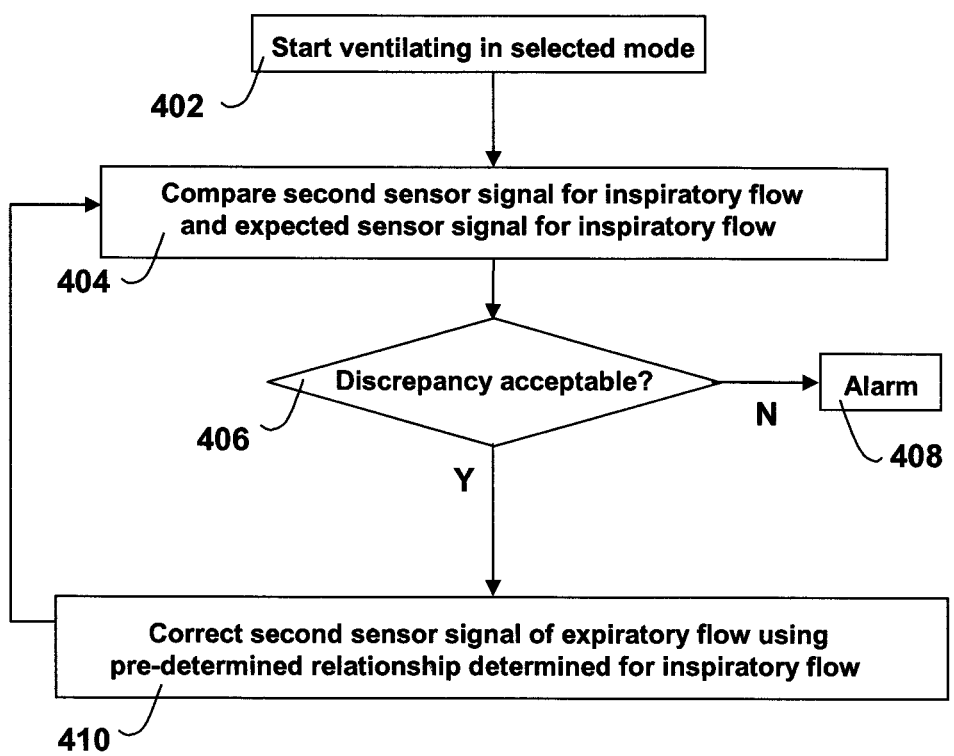
FIG. 4 is a process diagram.

FIG. 4 is a process diagram 400 illustrating an embodiment of a method in the invention, using the specific hose system 106. In a first step 402, the ventilating process is started in the selected ventilation mode. In a second step 404, the second sensor signal from the second sensor 112, measuring the inspiratory flow proximal to the patient 104, is compared to an expected sensor signal. The expected sensor signal is determined by the type of the hose system expected in the selected ventilation mode, and the first sensor signal from the first flow sensor 110. In a third step 406, it is determined if the discrepancy between the second sensor signal and the expected sensor signal is acceptable, e.g., within predetermined limits as represented by the parameter domain bounded by the curves 206 and 208 discussed above with reference to the diagram 200 of FIG. 2 and the diagram 300 of FIG. 3.

The second step 404 and/or the third step 406 may be initiated once the transients in the gas flow, occurring as a result of starting up the ventilating, have disappeared.

If the discrepancy is unacceptable, an audible or visual alarm is issued, in a fourth step 408, to a person attending the ventilating. As mentioned above, a significant discrepancy may indicate that a type of hose system is being used that is incompatible with the selected ventilation mode, or that the hose system used is malfunctioning as a result of, e.g., leakage or blockage. The attending person may then intervene.

If the discrepancy is acceptable, the process continues with a fifth step 410. For example, the first sensor signal is representative of the inspiratory flow. If the second sensor signal, also measured for the inspiratory flow, deviates from the expected sensor signal, but stays within a margin of +30% and −25% of the expected sensor signal, then the discrepancy between the second sensor signal and the expected sensor signal is acceptable. In the fifth step 410, the second sensor signal from the second flow sensor 112 is captured, now representative of the expiratory flow proximal to the patient 104. The fifth step 410 uses the predetermined relationship between the readings of the first flow sensor 110 and readings of the second flow sensor 112, both with regard to the inspiratory flow. This predetermined relationship enables to map the less accurate second sensor signal for the expiratory flow onto a more accurate value derived from a first sensor signal of the first flow sensor 110 that can be associated with the value of the second sensor signal. Note that the value of the first sensor signal relates to the inspiratory flow and that this value is used to correct the value of the second sensor signal relating to the expiratory flow.

After the fifth step 410, the process returns to the second step 404. The second step 404, the third step 406 and the fifth step 410 may form a loop that constitutes a recurrent process. For example, the process is executed during every breathing cycle of the patient, or after two or more breathing cycles. Alternatively, the process occurs once per time interval, e.g., once every 10 or 20 seconds, during the ventilating. Alternatively, the process is started each time when the flow of the respiratory gas reaches a certain level, or each time when the rate of change of the flow of the respiratory gas reaches a certain level.

While specific embodiments of the invention have been described in detail to illustrate the application of the principles of the invention, it will be understood that the invention may be embodied otherwise without departing from such principles.

What is claimed is:

1. A method of medically ventilating a patient via a hose system, the method comprising the steps of:
    selecting a predetermined ventilation mode from a plurality of predetermined ventilation modes;
    generating a respiratory flow according to the predetermined ventilation mode selected, the predetermined ventilation mode selected determining a type of hose system that should be used;
    generating a first sensor signal, indicative of an inspiratory flow distant from the patient, wherein a connected hose system is provided between the patient and the location from which the first sensor signal is generated;
    generating a further sensor signal indicative of the respiratory flow proximal to the patient, wherein the location from which the further sensor signal is generated is at the connected hose system, or is adjacent to the patient;
    determining an expected sensor signal, indicative of the respiratory flow proximal to the patient, on the basis of the first sensor signal and the predetermined ventilation mode selected, wherein the type of hose system that should be used establishes a pre-determined relationship between the first sensor signal and the expected sensor signal; and
    controlling the ventilating with a control action that depends on the expected sensor signal.

2. The method according to claim 1, wherein:
    the further sensor signal is representative of the inspiratory flow proximal to the patient; and
    the controlling comprises:
    determining a discrepancy between the further sensor signal and the expected sensor signal; and
    triggering an alarm for drawing attention to the discrepancy if the discrepancy has a magnitude larger than a predetermined threshold.

3. The method according to claim 1, wherein:
    the further sensor signal is representative of the expiratory flow proximal to the patient; and
    the controlling comprises:
    determining a discrepancy between the further sensor signal and the expected sensor signal; and
    if a magnitude of the discrepancy determined is acceptable according to a predetermined criterion, correcting, under control of the discrepancy, the further sensor signal for controlling the ventilating.

4. A medical ventilation device comprising:
    a ventilation controller configured to receive a selection of a predetermined ventilation mode from a plurality of predetermined ventilation modes to control the generation of a respiratory flow according to one of the plurality of predetermined ventilation modes selected for ventilating the patient, each of the predetermined ventilation modes determining a type of hose system that should be used;

a connected hose system configured to receive the respiratory flow;
a first flow sensor for generating a first sensor signal indicative of an inspiratory flow distant from the patient, wherein the connected hose system is provided between a patient end of the connected hose and the location of the first flow sensor;
a further flow sensor, the connected hose system comprising the further flow sensor for generating a further sensor signal indicative of the respiratory flow proximal to the patient;
an input for receiving the further sensor signal; and
a signal processing system configured for:
determining an expected sensor signal, indicative of the respiratory flow proximal to the patient, on the basis of the first sensor signal and the one of the plurality of predetermined ventilation modes selected, wherein the type of hose system that should be used establishes a pre-determined relationship between the first sensor signal and the expected sensor signal and the determination of the expected sensor signal is based on the established pre-determined relationship between the first sensor signal and the expected sensor signal; and
controlling the ventilating with a control action that depends on the expected sensor signal.

5. The medical ventilation device according to claim 4, further comprising an alarm unit coupled to the signal processing system, the alarm unit being configured for issuing an alarm to a human operator of the medical ventilation device, wherein:
the further sensor signal is representative of the inspiratory flow proximal to the patient;
the signal processing system is operative to activate the alarm unit if there is a discrepancy between the further sensor signal and the expected sensor signal, and if the discrepancy has a magnitude larger than a predetermined threshold.

6. The medical ventilation device according to claim 4, wherein:
the further sensor signal is representative of the expiratory flow proximal to the patient and the medical ventilation device; and
the signal processing system is operative to determine a discrepancy between the further sensor signal and the expected sensor signal; and
if a magnitude of the discrepancy determined is acceptable according to a pre-determined criterion, the signal processing system corrects the further sensor signal, under control of the discrepancy determined, and controls the ventilation controller in dependence on the corrected further sensor signal.

7. The medical ventilation device according to claim 4, further comprising a user interface for selection of the one of the plurality of predetermined ventilation modes.

8. A medical ventilation signal processing system comprising:
a ventilation controller configured to receive a selection of a predetermined ventilation mode from a plurality of predetermined ventilation modes to control the generation of a respiratory flow according to one of the plurality of predetermined ventilation modes for ventilating a patient, each of the predetermined ventilation modes determining a type of hose system that should be used;
a connected hose system configured to receive the respiratory flow;
a first flow sensor for generating a first sensor signal indicative of an inspiratory flow distant from the patient, wherein the connected hose system is provided between a patient end of the connected hose and the location of the first flow sensor;
a further flow sensor, the connected hose system comprising the further flow sensor for generating a further sensor signal indicative of the respiratory flow proximal to the patient; and
a determination means for determining an expected sensor signal, indicative of the respiratory flow proximal to the patient, on the basis of the first sensor signal and the predetermined ventilation mode selected, wherein the type of hose system that should be used establishes a pre-determined relationship between the first sensor signal and the expected sensor signal and the determination of the expected sensor signal is based on the established pre-determined relationship between the first sensor signal and the expected sensor signal, wherein the ventilation controller is configured to control ventilation of the patient with a control action that depends on the expected sensor signal.

9. The medical ventilation signal processing system according to claim 8, further comprising an alarm unit coupled to the determination means, the alarm unit being configured for issuing an alarm to a human operator of the medical ventilation device, wherein:
the further sensor signal is representative of the inspiratory flow proximal to the patient; and
the signal processing system is operative to activate the alarm unit if there is a discrepancy between the further sensor signal and the expected sensor signal, and if the discrepancy has a magnitude larger than a predetermined threshold.

10. The medical ventilation signal processing system according to claim 8, wherein:
the further sensor signal is representative of the expiratory flow proximal to the patient and the medical ventilation device; and
the determination means is operative to determine a discrepancy between the further sensor signal and the expected sensor signal; and
if a magnitude of the discrepancy determined is acceptable according to a pre-determined criterion, the determination means corrects the further sensor signal, under control of the discrepancy determined, and the controller controls ventilation in dependence on the corrected further sensor signal.

11. A physical data carrier device configured for use with a medical ventilation device configured for being coupled to a patient via a hose system for a respiratory flow according to a predetermined ventilation mode, the predetermined ventilation mode determining a type of hose system that should be used, for ventilating the patient with the medical ventilation device including a first flow sensor for generating a first sensor signal indicative of an inspiratory flow distant from the patient, wherein a connected hose system is provided between the patient and the location from which the first sensor signal is generated and the connected hose system comprises a further flow sensor for generating a further sensor signal indicative of the respiratory flow proximal to the patient and the medical ventilation device has an input for receiving the further sensor signal, the physical data carrier device comprising:
a data carrier; and
a data structure comprising data representative of a relationship between the first sensor signal and the expected sensor signal for signal processing to determine an expected sensor signal, indicative of the respiratory flow proximal to the patient, on the basis of the first sensor signal and the predetermined ventilation mode selected, wherein the type of hose system that should be used establishes a pre-determined relationship between the first sensor signal and the expected sensor signal and for controlling the ventilating with a control action that depends on the expected sensor signal.

* * * * *